United States Patent [19]

Moore et al.

[11] Patent Number: 4,773,417

[45] Date of Patent: Sep. 27, 1988

[54] METHOD FOR USING A TENDON STRIPPER AND LEADER SET

[76] Inventors: Robert R. Moore, 4010 East Ave., Hayward, Calif. 94542; Steve Lamb, 6724 Corte Del Vista, Pleasanton, Calif. 94566; Eugene M. Wolf, 3400 California St., 2nd Floor, San Francisco, Calif. 94118

[21] Appl. No.: 524

[22] Filed: Jan. 5, 1987

[51] Int. Cl.$^4$ ............................................. B61B 17/00
[52] U.S. Cl. ............................... 128/303 R; 128/92 V
[58] Field of Search ................. 128/92 V, 303 R, 305

[56] References Cited

FOREIGN PATENT DOCUMENTS 2747568  4/1979  Fed. Rep. of Germany ... 128/92 V

*Primary Examiner*—Michael H. Thaler
*Attorney, Agent, or Firm*—Bielen and Peterson

[57] ABSTRACT

A tendon stripper and leader set for stripping a tendon to a select diameter and engaging the stripped end with a tendon leader sized to the stripped tendon for positioning the tendon during bone attachment or other procedures. The tendon stripper is formed as an elongated tool with a handle, a long slender neck and a tip having a coiled eyelet with a stripping edge and a side entry slot, the tendon leader comprising an elongated semirigid leader with a woven expandable end sized to enlarge over the end of a stripped tendon on installation and contract around the tendon during tension for relocating the tendon.

3 Claims, 2 Drawing Sheets

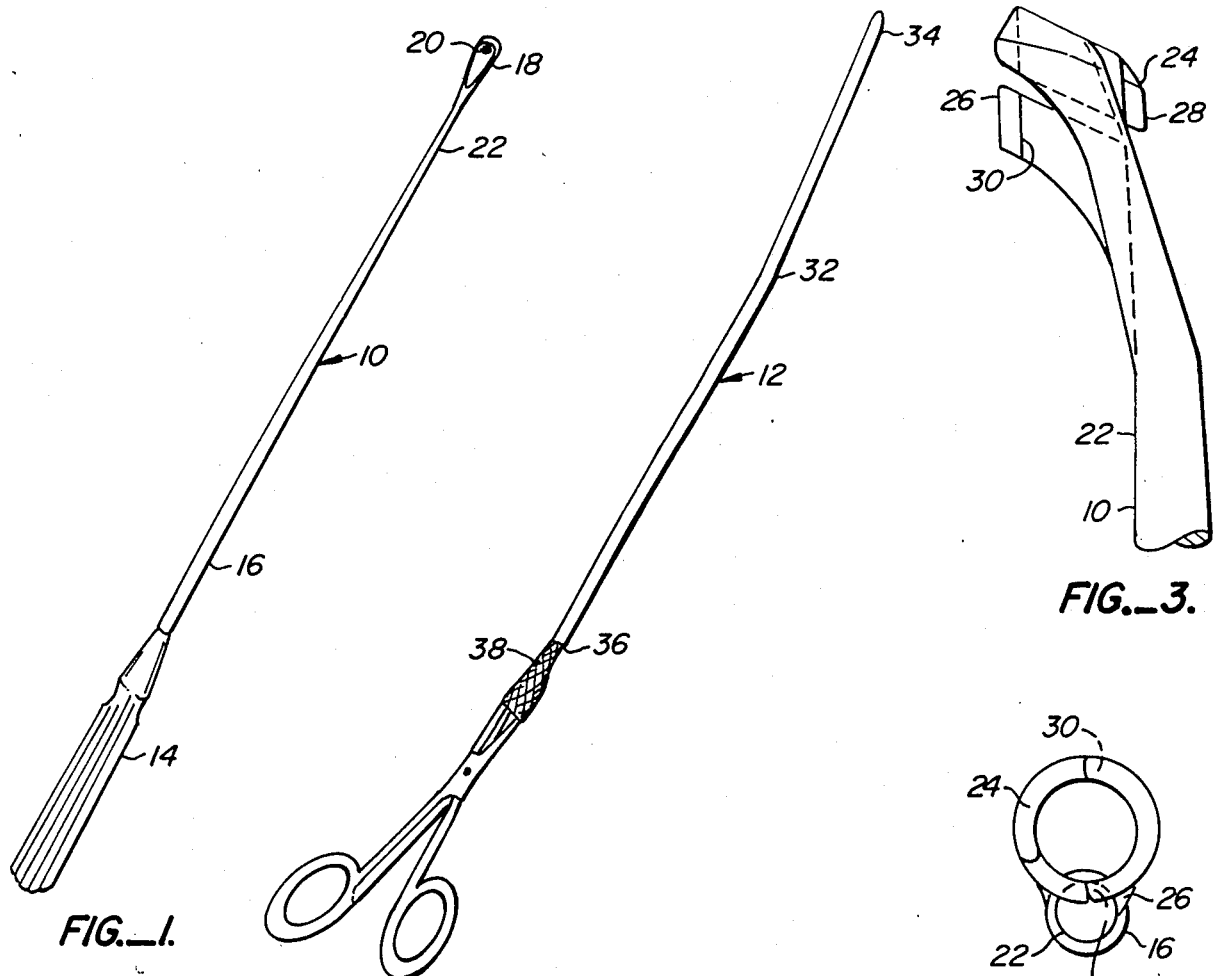
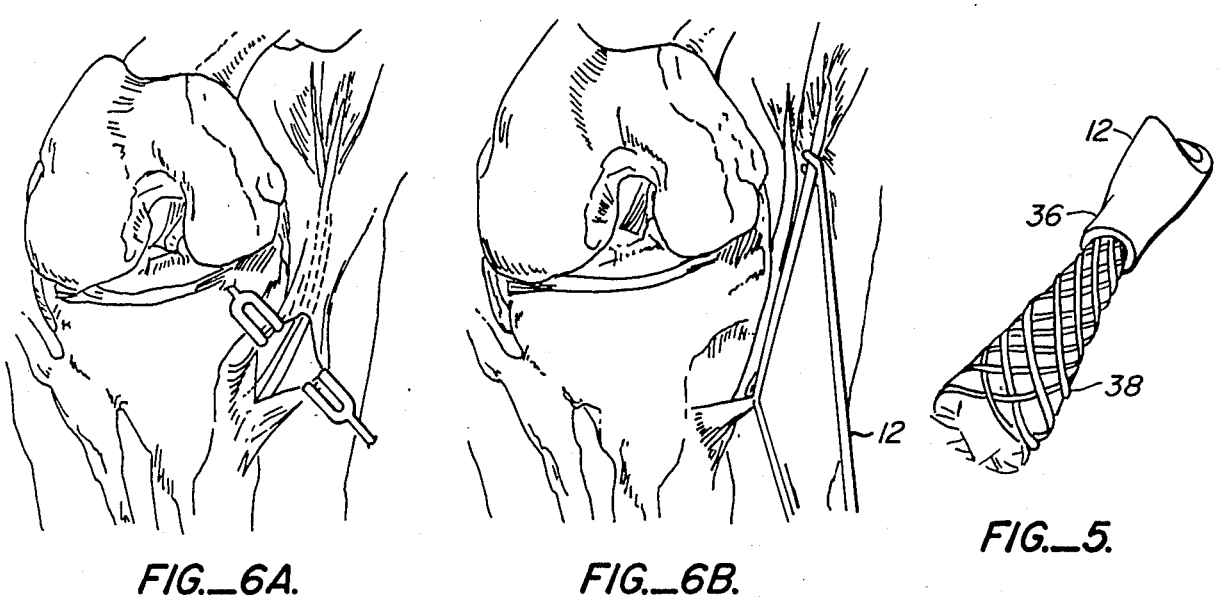

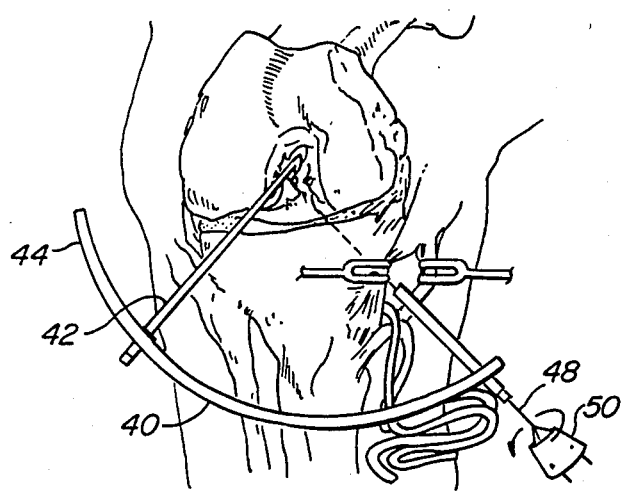
FIG._6C.
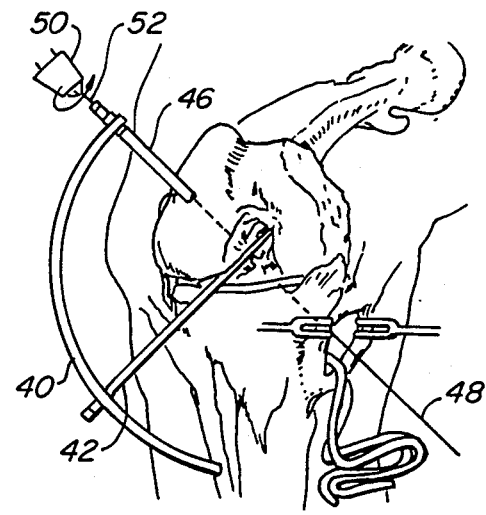
FIG._6D.
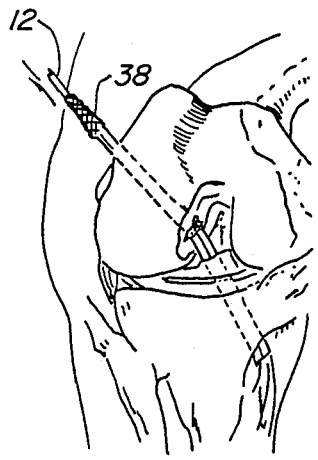
FIG._6E.
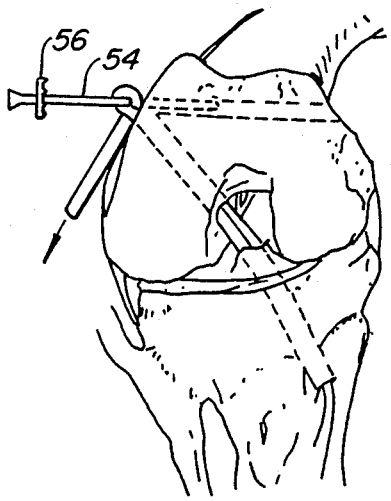
FIG._6F.

METHOD FOR USING A TENDON STRIPPER AND LEADER SET

BACKGROUND OF THE INVENTION

This invention relates to a cooperative tool and implement for sizing and relocating a tendon for arthrotomic or arthroscopic procedures, particularly repair procedures for torn or separated tendons, muscles and ligaments. The stripper tool isolates, sizes and strips a tendon preparatory to repair anchoring or relocation to a new site. The leader implement engages the end of a severed tendon, muscle or ligament and aids in locating the anatomical tissue structure to a desired site or position.

Prior tendon stripper have been constructed with a split eyelet presenting an incomplete circular eye with an entry slot generally aligned with the axis of the elongated neck of the instrument. The slot allows the tendon to be engaged with the eyelet by entry through the side slot. In stripping a tendon with the prior art device, the portion of the tendon aligned with the slot is unaffected on initial strokes, requiring the instrument to be periodically rotated to thoroughly strip the complete circumference of the tendon. While angling the slot improves the thoroughness of the stripping action, it makes the tendon more difficult to engage, necessitating an enlarged access incision for angularly orienting the instrument to align the slot with the tendon during engagement. Furthermore, the opportunity of the tendon to become disengaged from the stripper is substantially greater in prior art devices, particularly when the tendon is aligned with the slot or becomes aligned with the slot during stripping procedures.

Customarily, a tendon leader is used in conjunction with a tendon stripper. Prior tendon leaders have been constructed when the tendon end is sutured to a semi rigid leader. Because a smooth transition between the tendon and the leader is difficult to construct, the end of the tendon may snag causing the separation of the tendon from the leader.

The tendon leader and tendon stripper of this invention provide a tool and implement for a new method of stripping and locating a tendon. The devices are usable in different sizes for a variety of arthrotomic and arthoscopic procedures, particularly repair or reconstruction procedures for damaged or torn ligaments, muscles or tendons, where tendons are prepared for reseating or relocation. The tools, particularly the tendon leader, may be used in other unrelated medical procedures for positioning vessels and other tubular or tendenous anatomical tissue structure.

SUMMARY OF THE INVENTION

This invention relates to a cooperative tendon stripping tool and tendon positioning device for arthroscopic or arthrotomic procedures. The tendon stripping tool is an elongated instrument with a handle, a long neck and a tip having a helical configured eyelet with a side entry for engaging and isolating a tendon, and, stripping he outer surface tissue to form a relatively uniform strand for relocation and attachment. Once the tendon is stripped and one portion of it is severed, the tendon positioning device is employed to position the tendon, generally for anchoring to a bone.

The positioning device is a tendon leader that in its preferred form is a slender, nonelastic, but bendable instrument with an end having grasping means for engaging and gripping the end of the tendon for pulling and stretching the tendon to locate the tendon in the desired position with the desired tension. The tendon leader and stripping tool are compatibly sized for a particular tendon being prepared ranging from the larger tendons of the knee to the smaller tendons of the fingers.

The tendon stripper and tendon leader may have use in other procedures and on other anatomic components than as described with reference to a particular method for repair of a torn anterior cruciate ligament as described herein.

The cooperative use of the tendon stripper and tendon leader are described in detail in the detailed description of the preferred embodiment and method.

The tendon stripper and leader are particularly adaptable to the reconstruction of a torn anterior crucite ligament. The implements enable a reconstruction by arthroscopic techniques minimizing the trauma to the knee from more extensive surgical procedures. Both the tendon stripper and the leader are of selected size for the tendons utilized for relocation. It is understood that reconstruction procedures for other tendons or for the tendons of children may require differently sized tools or implements, although the leader, being expendable, is suitable for a range of tendon diameters.

BRIEF DESCRIPTION OF THE DRAWINGS

FIG. 1 is a perspective view of the tendon stripper tool.

FIG. 2 is a perspective view of the tendon leader implement.

FIG. 3 is an enlarged side view partially fragmented of the tip of the tendon stripper.

FIG. 4 is an end view of the tip of the tendon stripper shown in FIG. 3.

FIG. 5 is an enlarged end view, partially fragmented of the end of the tendon leader implement.

FIG. 6A is a schematic perspective view of a procedural step in relocation of a torn anterior crucite ligament.

FIG. 6B is a view of a subsequent step in the procedure of FIG. 6A.

FIG. 6C is a view of a subsequent step in the procedure of FIG. 6A.

FIG. 6D is a view of a subsequent step in the procedure of FIG. 6A.

FIG. 6E is a view of a subsequent step in the procedure of FIG. 6A.

FIG. 6F is a view of a subsequent step in the procedure of FIG. 6A.

DETAIL DESCRIPTION OF THE PREFERRED EMBODIMENT AND METHOD.

The tendon stripper 10 and tendon leader 12 are shown respectively in the FIGS. 1 and 2 of the drawings. The drawing figures include a sequence for employing the instruments with other auxiliary components in a procedure for performing an arthroscopic reconstruction of a torn anterior cruciate ligament.

Referring to FIG. 1 the tendon stripper 10 is shown having a handle 14 with an elongated slender shank 16 with a specialty tip 18. The tip 18 is uplifted to form an eyelet 20 with a sight that clears the proximal tapered end portion 22 of the shank. The eyelet as shown in FIGS. 3 and 4. is formed by two, oppositely disposed, counter rotated tines 24, 26 that helically wrap around a common axis at a fixed radius from the axis. The tines are displaced from each other with terminal ends 28, 30, respectively, that circumferentially overlap. The displacement enables the lead tine 24, which is most distal from the shank to engage a tendon, and by rotating the shank entrain the tendon in the eyelets. The deformable tendon easily slips in the narrow slot between the tines.

The stripper design eliminates the necessity of severing the tendon and threading the tendon through an eyelet. Using the devised stripper the tendon remains firmly attached at both ends for the stripping procedure.

The leading edge of the leading tine is prepared to a given sharpness of 0.03 millimeter radius on 30° edge. The leading edge of the counterrotated trailing tine is dulled except proximate its initiation wherein it has a similarly prepared edge to cover the circumferential sector missed by the lead tine. In this manner the entire circumference of the tendon is engaged and stripped by the two prepared edges. The prepared edges have a sharpness sufficient to scrape, but not slice or cut the tendon during the forward motion of the stripper longitudinal to the tendon. Furthermore, the overlapping trailing tine prevents the stripper from inadvertently dislodging from the tendon during the stripping strokes.

In many procedures, the tendon leader 12 is used in conjunction with the tendon stripper to facilitate relocation of the tendon, particularly through a drilled tunnel. The tendon leader 12 is constructed with a relatively stiff stem 32 which in the preferred embodiment is deformable such that various curved or bent configurations can be devised according to the task to be performed or passage to be followed. In the embodiment shown the stem is substantially cylindrical in configured with a blunt lead end 34. The stem may advantageously be tapered with a rigid pointed end where an original passage must be formed. The trailing end 36 has a fiber web 38 extending beyond the stem 36. The stem is a vinyl shrink-tube that is thermally shrunk-fit over the web. As shown in the enlarged view of FIG. 5, the fibers 40 of the web are nylon monofillament, chemically inert and arranged are arranged in a cross-weave diagonally oriented to the axis of the elongated stem. This construction and arrangement enables the tubular web 38 to be expanded in diameter for insertion of a tendon by using a hemostat as shown in FIG. 2. The hemostat 40 is used first to stretch the opening and then to grasp and insert the end of the tendon into the web. The end of the tendon is sutured to the web to prevent inadvertent dislodgement. When tension is applied to the tendon leader the web contracts around the tendon in the manner of a Chinese finger lock enabling the tendon leader to draw the tendon along the path of the leader. The tendon leader can be passed through a bored or pierced tunnel of minimal dimension without disengaging the attached tendon. Furthermore, the construction grip facilitates application of a final tension to the tendon during anchoring procedures. A unique procedure for a torn anterior crucite ligament is described in FIGS. 6A-6F.

In the knee reconstruction involving a torn anterior crucite ligament (ACL), the procedure begins with an arthrosopic debridement of the torn ACL and fat pad to clear the intercondylar notch. A two inch incision is made over the pes anserinus and the satorius is split to reveal the semitendinosis and gracilis tendons as shown in FIG. 6A. The tendons are detached from the muscle using the specialized stripper while the tendons remain anchored at each end as shown in FIG. 6B. The tendons should be freed of any distal facial expansions by sharp dissection prior to stripper use. Tension is placed on the tendon by the index finger of one hand while the stripper is carefully directed by the other. Stripping is accomplished by engaging each tendon in the tip through the gap by partial rotation of the shank. Once engaged, the stripper circumferentially debrides the tendon using the leading edge of the eyelet 20 as shown in FIG. 6B. In this manner the length of each tendon is maximized before the distal end is severed for relocation.

To relocate, a passage must be formed through the tibia and also through the femur that coincide at the former site of the ACL. This is accomplished by an arcuate drill guide 40 which includes a pointed position pin 42 that is inserted into the joint such that the end is located in the intercondylar notch as shown in FIG. 6C. The position pin 42 is adjustably mounted in a central slot (not visible) in the arcuate member 44 of the guide. In this manner, the arcuate member can be tracked on the pin to position a drill sight 46 mounted at the end of the arcuate member at the position desired. Since the drill sight 46 is radially oriented relative to the arcuate member, it sights to a single centerpoint regardless how the arcuate member is tracked or pivoted on the position pin.

Using the drill guide as shown in FIG. 6C a k-wire 48 is drilled up through the medial tibial plateau from a point just proximal to the pes insertions and anterior to the medial collateral ligament. A 2-inch incision is made over the lateral condylar flare. The iliotibial band is split and the vastus lateralis is retracted. The drill sight 46 is adjusted to position the drill 50 for entry at the desired anchoring point on the femoral condyle. As shown in FIG. 6D the drill guide 40 sights the femoral isometric point in the intercondylar notch and a k-wire 52 is drilled to such point, meeting the end of the previously drill wire.

The k-wire positions are checked and a tunnel is drilled over the inserted k-wires in both the tibia and femur using a cannulated drill bit. The distal end of each stripped tendon is severed and prepared, removing any residual muscle tissue. The tendon ends are sutured together and inserted into the end of the tendon leader where further suturing secures the tendon to the netting or web of the leader. The end of the leader is fed up through the tibial tunnel and guided into the femoral tunnel. Upon exiting the femoral tunnel it is pulled to draw the attached tendon up through the interconnected tunnels, as shown in FIG. 6E. The gripped tendon ends are pulled up through the tunnels and with tension on the tendons are secured with a screw 54 and ligament washer 56 to the femoral condyle proximate the tunnel end as shown in FIG. 6F.

The relocated semitendinosis and gracilis tendons provide an anteria cruciate ligament graft with minimal trauma to the knee and maximal likelihood of successful functioning.

While the implements described, in particular the tendon stripper and tendon leader are particularly adapted to the procedure described, it is apparent that with appropriate compatibility in sizing, such implements can be adapted for usage in many other surgical procedures.

While in the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A method of repairing a torn anterior crucite ligament comprising the steps of:
   a. arthroscopically debriding the torn anterior crucite ligament and fat pad, making an incision over the pes anserinus;
   b. splitting the satorius;
   c. stripping the semitendexiosis and gracilis tendons from connected muscle;
   d. detaching tendons at their upper ends;
   e. drilling a passage to the intercondylar notch through the medial tibial plateau from a point proximal the pes insertions and the anterior to the medial collateral ligament;
   f. making an incision over the lateral condylar flare;
   g. splitting the iliotibial band and retracting the vastus lateralis;
   h. drilling a passage down through the lateral femoral condyle to the intercondylar notch;
   i. inserting the semitendinosis and gracilis tendons up through the drilled passages using a connected tendon leader;
   j. securing the tendons to the lateral femoral condyle.

2. The method of claim 1 wherein the step of stripping the semitendinosis and gracilis tendons is performed with a tendon stripper having an elongated slender shank with a tip with a helically configured eyelet having an entry slot for engaging the tendon, and on rotation of the tool, encircling the eyelet enabling a reciprocal motion to strip the tendons from the connecting muscle.

3. The method of claim 1 wherein the step of inserting the semitendinosis and gracilis tendons up through the drilled passages is performed with a tendon leader having an elongated stem with a longitudinal axis, the stem being at least semirigid in construction and having a lead end and a trailing end, wherein the trailing end has connected thereto a tube of fibrous web material fashioned with a cross-weave diagonally oriented to the longitudinal axis of the elongated stem, said tube being constructed for insertion and engagement of the ends of the severed semitendinosis and gracilis tendons prior to passing the lead end of the leader up through the drilled passages.

* * * * *